United States Patent [19]

Berlin

[11] 4,327,361
[45] Apr. 27, 1982

[54] GAS SENSOR

[75] Inventor: Howard M. Berlin, Newark, Del.

[73] Assignee: The United States of America as represented by the Secretary of the Army, Washington, D.C.

[21] Appl. No.: 204,444

[22] Filed: Nov. 6, 1980

[51] Int. Cl.³ .............................................. G08B 17/10
[52] U.S. Cl. ...................................... 340/634; 422/98
[58] Field of Search ....................... 340/634, 633, 632; 73/23 R, 27 R; 331/65; 422/97, 98; 23/232 E

[56] References Cited

U.S. PATENT DOCUMENTS

| | | | |
|---|---|---|---|
| 3,686,655 | 8/1972 | Kasahara | 340/634 |
| 3,860,919 | 1/1975 | Aker | 340/634 |
| 3,950,739 | 4/1976 | Campman | 340/634 |
| 4,104,619 | 8/1978 | Hesler | 340/629 |
| 4,109,240 | 8/1978 | Scheidweiler | 340/629 |
| 4,185,491 | 1/1980 | Owen | 340/634 |

Primary Examiner—John W. Caldwell, Sr.
Assistant Examiner—Daniel Myer
Attorney, Agent, or Firm—Nathan Edelberg; Robert P. Gibson; Max Yarmovsky

[57] ABSTRACT

A variable resistance gas sensor controls the output frequency of a variable frequency tone generator. A tone decoder monitors the output frequency of the tone generator. When the gas concentration attains a predetermined threshold value, the tone decoder produces an output signal which activates a latch circuit to energize an alarm device. The latch circuit continues to energize the alarm device even after the gas concentration is reduced below the threshold value until manually reset.

11 Claims, 2 Drawing Figures

GAS SENSOR

GOVERNMENTAL INTEREST

The invention described herein may be manufactured, used and licensed by or for the Government for governmental purposes without the payment to me of any royalty thereon.

BACKGROUND OF THE INVENTION

The present invention relates to gas sensors and more particularly to gas sensors employing a variable resistance gas sensing element.

Semiconductor gas sensors are known which change their resistance in response to the presence of gas molecules on their surfaces. A gas sensor such as, for example, a Taguchi Gas Sensor (TGS sensor hereinafter) manufactured by Figaro Engineering, Inc., Osaka, Japan, includes a semiconductor surface with an integral heater element to maintain appropriate operating conditions. The resistance between terminals of a TGS sensor is determined by the number of free carriers in the semiconductor material. When a gas molecule is absorbed on the surface of the semiconductor, it may bind a free carrier to reduce the conductivity thereof. When a TGS sensor is normally exposed to air, absorbed oxygen increases the resistance of the material to a substantially constant value. When a TGS sensor is exposed to other gases such as natural and other combustible gases, alcohol, ketone, ester and benzol families, as well as certain toxic gases, the resistance thereof decreases from its value in air. Such a TGS sensor may typically exhibit a maximum resistance in clean air of 100K ohms which may decrease to as low as 10K ohms in the presence of an appropriate concentration of various gases.

Prior methods of detecting gas concentration using TGS sensors have included detecting a change in current through it. Such sensing techniques have the disadvantage that a sudden change in power supply or reference voltage changes the operating characteristics of the detecting circuit and either produces a false detection or fails to produce a detection when it should.

OBJECTS AND SUMMARY OF THE INVENTION

Accordingly, it is an object of the present invention to provide a gas sensing apparatus which overcomes the drawbacks of the prior art.

It is a further object of the invention to provide a gas sensing apparatus which is relatively insensitive to power supply and reference voltage variations.

It is a further object of the present invention to provide a gas sensing apparatus using a variable resistance gas sensing element which controls the frequency of a variable frequency tone generator. A tone decoder is employed to monitor the frequency output of the variable frequency tone generator and, when the frequency reaches a value which is indicative of a certain gas concentration, the tone decoder provides an output which is effective to operate a latching alarm device. The latching alarm device thereupon provides a constant alarm signal until reset even after the gas concentration which caused the alarm to occur has dissipated.

It is an aspect of the present invention to provide a gas sensor comprising a gas sensing element operative to change an electrical characteristic thereof in response to a gas, means for generating a tone having a frequency which is variable in response to the electrical characteristic, means for sensing the tone and for producing an output signal in response thereto when the frequency reaches a predetermined value, and means for producing an alarm in response to the output signal.

The above, and other objects, features and advantages of the present invention will become apparent from the following description read in conjunction with the accompanying drawings, in which like reference numerals designate the same elements.

DETAILED DESCRIPTION OF THE PREFERRED EMBODIMENT

Figure 1:
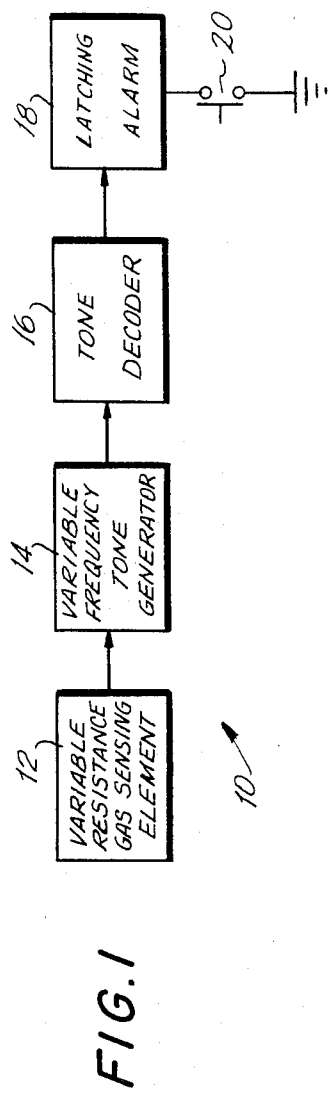
FIG. 1 is a simplified block diagram of a gas sensor according to an embodiment of the present invention.

Referring now to FIG. 1, there is shown, generally at 10, a gas sensor according to an embodiment of the present invention. A variable resistance gas sensing element 12 which may be a TGS sensor, varies the resistance at an input of a variable frequency tone generator 14. Variable frequency tone generator 14 generates a frequency which is variable in dependence on the resistance of gas sensing element 12.

The frequency generated by variable frequency tone generator 14 is applied to an input of a tone decoder 16. Tone decoder 16 responds to a particular band of frequencies by producing an output signal which is applied to a latching alarm 18. When latching alarm 18 receives the output signal of tone decoder 16, it produces an alarm signal which may be arranged to continue after the input from tone decoder 16 is removed. A reset switch 20 may be actuated to reset, or inactivate, latching alarm 18 to prepare it for a new sensing cycle.

Figure 2:
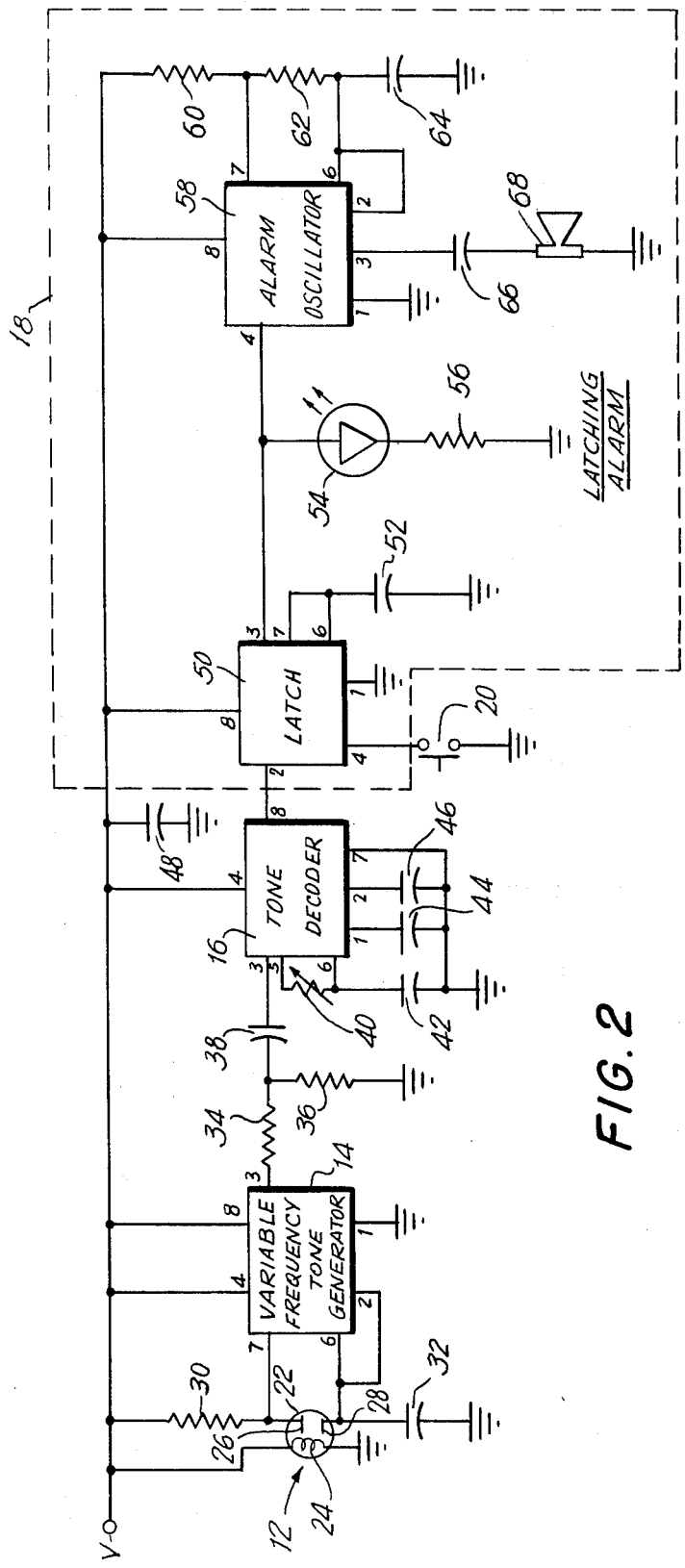
FIG. 2 is a schematic diagram of one circuit for implementing the apparatus of FIG. 1.

Referring now to FIG. 2, variable resistance gas sensing element 12 is seen to include a Taguchi Gas Sensor (TGS) 22 having a resistance heater 24 and first and second electrodes 26 and 28.

A supply voltage V is connected through resistance heater 24 to ground to elevate the temperature of TGS 22 to a suitable value such as, for example, 200° to 400° C. Supply voltage V is also connected through a resistor 30 to electrode 26 of TGS 22 and to an input of variable frequency tone generator 14. Electrode 28 of TGS 22 is connected through a capacitor 32 to ground and to inputs of variable frequency tone generator 14.

Although any suitable circuit may be employed in variable frequency tone generator 14, in the preferred embodiment, variable frequency tone generator 14 is an NE555 or SE555 linear integrated circuit timer. The pin identification adjacent inputs and outputs of variable frequency tone generator 14 are referenced to the standard pinout of these circuits.

Any suitable frequency range may be employed by appropriate selection of resistor 30 and capacitor 32. When the resistance of resistor 30 is about 1K ohms and the capacitance of capacitor 32 is about 0.01 microfarads, the output frequency of variable frequency tone generator 14 may be controlled in the range of from about 1.4 KHz to 14 KHz by variation in the quantity of gas to which TGS 22 is exposed.

The output frequency of variable frequency tone generator 14 is applied to a voltage divider consisting of resistors 34 and 36. The resulting signal at the junction of resistors 34 and 36 is AC coupled through a capacitor 38 to an input of tone decoder 16.

Although any appropriate integrated circuit or discrete component circuit may be employed for tone decoder 16, in the preferred embodiment, tone decoder 16 is a monolithic tone decoder such as a commercially available XR-567 (or NE-567 equivalent) monolithic tone decoder. The pin identifications adjacent inputs and outputs of tone decoder 16 are referenced to the standard pinout of an XR-567 monolithic tone decoder.

A variable resistor 40 between pins 5 and 6 of tone decoder 16 and a capacitor 42 between pin 5 and ground determine the threshold frequency of tone decoder 16, that is, the frequency at which tone decoder 16 changes its output at pin 8 from a high voltage to a low voltage. Capacitors 44 and 46 are conventionally employed for filtering.

A capacitor 48, connected from supply voltage V to ground reduces electrical noise which may be produced by latching alarm 18.

The output of tone decoder 16 is applied to a latch 50 in latching alarm 18. Latch 50 may be any suitable device such as, for example, a monostable multivibrator, a stepping relay, or a sustaining relay but, in the preferred embodiment, latch 50 is an NE555 or an SE555 linear integrated circuit timer. The pin identifications adjacent inputs and outputs of latch 50 are referenced to the standard pinouts of a 555 timer.

Pins 6 and 7 of latch 50 are jumpered together and are connected through a capacitor 52 to ground. When the low signal is received at pin 2 of latch 50 from tone decoder 16, output pin 3 of latch 50 goes high to indicate an alarm condition. Latch 50 remains in this triggered condition with a high output at pin 3 until reset by actuation of reset switch 20 connected between pin 4 and ground.

The high output pin 3 of latch 50 is applied to an input of a visual alarm device such as, for example, a light emitting diode 54 whose other terminal is connected through a resistor 56 to ground. Upon receiving the high output from latch 50, light emitting diode 54 is illuminated to indicate an alarm condition.

The high output of latch 50 is also applied to an input of an alarm oscillator 58. Alarm oscillator 58 may employ any suitable integrated or discrete circuit therein. In the preferred embodiment, alarm oscillator 58 is an NE555 or SE555 linear integrated circuit timer. The pin identifications adjacent inputs and outputs of alarm oscillator 58 are referenced to the standard pinout of a 555 timer. Resistors 60 and 62 and capacitor 64 set the frequency and duty cycle of an output signal at pin 3 of alarm oscillator 58. The output signal is applied through a capacitor 66 to an audible alarm device such as a loud speaker 68, the other terminal of which is connected to ground.

Although both visual and audible alarm devices are provided in latching alarm 18, it should not be assumed that the presence of both are required for the present invention. In fact, other alarm means may be substituted therefor such as, for example, mechanical annunciators or radio transmitters transmitting RF alarm signals to remote locations.

Having described specific embodiments of the invention with respect to the accompanying drawings, it is to be understood that the invention is not limited to those precise embodiments, and that various changes and modifications may be effected therein by one skilled in the art without departing from the scope or spirit of the invention as defined in the appended claims.

What is claimed is:

1. A gas sensor comprising:
   sensing means for generating a varying output impedance as a function of the concentration of gases to which it is exposed, said sensing means including heater means for elevating said sensing means to a specific temperature range;
   voltage supply means for supplying energy to said heater means;
   a first resistor element operatively coupled to a first output terminal of said gas sensing means and to said voltage supply means;
   a first capacitor element operatively connected to a second output terminal of said sensing means and to a ground connection;
   linear integrated circuit timer means, having input terminal operatively coupled to said first resistor element and to said first capacitor element, said first resistor and capacitor having impedances selected to control the frequency of the output of said linear integrated timer means so that it is in the audio range;
   voltage divider means operatively coupled to the output of said timer means for reducing the voltage from the output of said timer means;
   a second capacitor electrically coupled to a common junction of said voltage divider means;
   tone decoder circuit means having an input terminal electrically AC coupled to said second capacitor;
   a variable resistor, electrically coupled to other adjacent input terminals of said tone decoder means;
   capacitor means electrically coupled intermediate said ground connection and said variable resistor for cooperating therewith for filtering the input of said tone decoder means;
   latch means electrically coupled to the output of said tone decoder means for generating a high output signal in response to a low signal from said tone decoder means, and for remaining at a high output state until reset;
   a reset switch electrically coupled to said latch means and said ground connection, for resetting said latch means from said high output state to a low output state;
   visual indicator means electrically coupled to the output of said latch means for visually indicating when said latch means generates a high output signal;
   oscillator means electrically connected to the output of said latch means for generating an output signal of a specific frequency and duty cycle when said latch means is generating said high output signal, and for producing no signal when said latch means is at said low output state;
   means for varying said specific frequency and duty cycle of said oscillator means; and
   alarm means electrically coupled to the output of said oscillator means for generating a signal when said visual indicator means is responsive to said latch means.

2. A gas sensor as recited in claim 1 wherein said sensing means includes a Taguchi Gas Sensor and said heater means is elevated to a temperature range of 200° to 400° C.

3. A gas sensor as recited in claim 2 wherein said timer means generates a variable frequency output signal in the audio range of 1.4 KHz to 14 KHz.

4. A gas sensor as recited in claim 3 wherein said decoder means includes a monolithic tone decoder.

5. A gas sensor as recited in claim 3, or 4 wherein said latch means includes a monostable multivibrator.

6. A gas sensor as recited in claim 5 wherein said latch means includes a stepping relay.

7. A gas sensor as recited in claim 6 wherein said latch means includes a NE555 linear integrated circuit timer.

8. A gas sensor as recited in claim 7 wherein said visual indicator means includes a light emitting diode.

9. A gas sensor as recited in claim 8 wherein said means for varying said specific frequency duty cycle of said oscillator means includes resistance and capacitance impedance means electrically coupled thereto.

10. A gas sensor as recited in claim 9 wherein said alarm means includes,
- a second capacitor having one terminal electrically coupled to an output terminal of said oscillator means; and
- a loud speaker electrically coupled to the other terminal of said second capacitor and connected in series with said ground connection.

11. A gas sensor as recited in claim 10 wherein said alarm means includes transmitting means for sending RF signals to a remote location.

* * * * *